US010989700B2

(12) United States Patent
Aratani et al.

(10) Patent No.: US 10,989,700 B2
(45) Date of Patent: Apr. 27, 2021

(54) TEMPERATURE HISTORY INDICATOR

(71) Applicant: Hitachi, Ltd., Tokyo (JP)

(72) Inventors: Sukekazu Aratani, Tokyo (JP); Hiroshi Sasaki, Tokyo (JP); Toyotaka Yuasa, Tokyo (JP); Kohhei Aida, Tokyo (JP); Yasuhiko Tada, Tokyo (JP); Masahiro Kawasaki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 587 days.

(21) Appl. No.: 15/747,794

(22) PCT Filed: Jul. 22, 2016

(86) PCT No.: PCT/JP2016/071476
§ 371 (c)(1),
(2) Date: Jan. 26, 2018

(87) PCT Pub. No.: WO2017/038292
PCT Pub. Date: Mar. 9, 2017

(65) Prior Publication Data
US 2018/0217114 A1 Aug. 2, 2018

(30) Foreign Application Priority Data
Sep. 3, 2015 (JP) .............................. JP2015-173435

(51) Int. Cl.
*G01N 31/22* (2006.01)
*G01K 11/16* (2021.01)
(Continued)

(52) U.S. Cl.
CPC ......... *G01N 31/229* (2013.01); *B32B 29/002* (2013.01); *G01K 3/04* (2013.01);
(Continued)

(58) Field of Classification Search
CPC ...... G01N 31/229; G01N 33/02; G01N 33/15; G01K 3/04; G01K 11/18; G01K 11/16;
(Continued)

(56) References Cited

U.S. PATENT DOCUMENTS 4,028,118 A * 6/1977 Nakasuji .............. C08K 5/0041
106/31.19
4,720,301 A * 1/1988 Kito ....................... B41M 5/305
106/31.17
(Continued)

FOREIGN PATENT DOCUMENTS

EP 1 972 913 A1 9/2008
JP 7-27633 A 1/1995
(Continued)

OTHER PUBLICATIONS

Japanese-language Office Action issued in counterpart Japanese Application No. 2017-537645 dated Dec. 11, 2018 with English translation (eight (8) pages).
(Continued)

*Primary Examiner* — Nimeshkumar D Patel
*Assistant Examiner* — Tania Courson
(74) *Attorney, Agent, or Firm* — Crowell & Moring LLP

(57) ABSTRACT

A purpose of the present invention is to provide a temperature history indicator that allows for visual confirmation of whether the temperature is at or below a prescribed temperature as well as simple conversion of this information into data. A temperature history indicator according to the present invention is characterized by being provided with a label layer and a temperature-indicating layer laminated above or below the label layer, wherein the temperature-indicating layer includes a substance having at crystalliza-
(Continued)

tion starting temperature of 10° C. or lower and a melting point at least 20° C. higher than the crystallization starting temperature.

10 Claims, 17 Drawing Sheets

(51) Int. Cl.
| | |
|---|---|
| *G01K 3/04* | (2006.01) |
| *G01K 11/12* | (2021.01) |
| *B32B 29/00* | (2006.01) |
| *G01K 11/18* | (2006.01) |
| *G01N 33/02* | (2006.01) |
| *G01N 33/15* | (2006.01) |

(52) U.S. Cl.
CPC .............. *G01K 11/12* (2013.01); *G01K 11/16* (2013.01); *G01K 11/18* (2013.01); *G01N 33/02* (2013.01); *G01N 33/15* (2013.01); *B32B 2250/03* (2013.01); *B32B 2255/12* (2013.01); *B32B 2323/04* (2013.01); *B32B 2519/00* (2013.01)

(58) Field of Classification Search
CPC ... G01K 11/12; B32B 29/002; B32B 2250/03; B32B 2255/12; B32B 2323/04; B32B 2519/00; B32B 27/36; B32B 15/085; B32B 15/09; B32B 3/08; B32B 7/05; B32B 27/10; B32B 2307/732; B32B 2307/40; B32B 2250/44; B32B 2255/10; B32B 2307/414; B32B 2307/412; B32B 2307/75; B32B 2307/71; B32B 2307/714; B32B 2307/4023; B32B 2307/4026; B32B 27/08; B32B 27/06; B32B 27/32
See application file for complete search history.

(56) References Cited

U.S. PATENT DOCUMENTS

| | | | | |
|---|---|---|---|---|
| 4,732,810 A * | 3/1988 | Kito | ............... | G01K 11/16 |
| | | | | 106/31.17 |
| 5,057,434 A * | 10/1991 | Prusik | ............... | B65D 79/02 |
| | | | | 116/207 |
| 5,161,233 A * | 11/1992 | Matsuo | ............... | G03G 5/02 |
| | | | | 355/77 |
| 5,490,956 A | 2/1996 | Kito et al. | | |
| 5,667,303 A * | 9/1997 | Arens | ............... | G01K 3/04 |
| | | | | 116/219 |
| 5,721,059 A * | 2/1998 | Kito | ............... | C08K 5/0008 |
| | | | | 252/583 |
| 5,919,404 A * | 7/1999 | Fujita | ............... | B41M 5/287 |
| | | | | 106/31.23 |
| 6,514,462 B1 * | 2/2003 | Simons | ............... | G01K 3/04 |
| | | | | 116/206 |
| 6,706,218 B2 * | 3/2004 | Lucht | ............... | C08G 61/126 |
| | | | | 116/201 |
| 7,332,109 B2 * | 2/2008 | Senga | ............... | B41M 5/28 |
| | | | | 252/582 |
| 7,829,162 B2 * | 11/2010 | Eskra | ............... | B41M 5/385 |
| | | | | 428/32.69 |
| 7,879,415 B2 * | 2/2011 | Hoshino | ............... | G02B 5/287 |
| | | | | 428/29 |
| 7,943,063 B2 * | 5/2011 | Lucht | ............... | G01K 11/16 |
| | | | | 252/408.1 |
| 8,343,437 B2 * | 1/2013 | Patel | ............... | G01K 3/04 |
| | | | | 422/424 |
| 8,395,504 B2 * | 3/2013 | Furuichi | ............... | G06K 19/0776 |
| | | | | 340/568.1 |
| 8,968,863 B2 * | 3/2015 | Brown | ............... | B32B 3/26 |
| | | | | 428/304.4 |
| 9,085,192 B2 * | 7/2015 | Clayton | ............... | C09J 7/30 |
| 9,592,694 B2 * | 3/2017 | Clayton | ............... | G01D 7/005 |
| 9,695,329 B2 * | 7/2017 | Ono | ............... | C09B 67/009 |
| 10,005,304 B2 * | 6/2018 | Clayton | ............... | B41M 5/287 |
| 10,239,336 B2 * | 3/2019 | Philippe | ............... | B41M 5/3372 |
| 10,378,970 B2 * | 8/2019 | Diehn | ............... | G01K 1/08 |
| 10,451,595 B2 * | 10/2019 | Patel | ............... | G07C 1/00 |
| 2006/0032427 A1 | 2/2006 | Ishii et al. | | |
| 2008/0043804 A1 * | 2/2008 | Goldsmith | ............... | G09F 3/0291 |
| | | | | 374/106 |
| 2008/0232427 A1 | 9/2008 | Leute et al. | | |
| 2009/0320742 A1 | 12/2009 | Leute et al. | | |
| 2012/0104743 A1 * | 5/2012 | Mehta | ............... | C09D 11/50 |
| | | | | 283/95 |
| 2012/0305637 A1 | 12/2012 | Nemet et al. | | |
| 2013/0152848 A1 * | 6/2013 | Lucht | ............... | C09D 11/50 |
| | | | | 116/201 |
| 2016/0089923 A1 * | 3/2016 | Philippe | ............... | B42D 25/378 |
| | | | | 283/67 |

FOREIGN PATENT DOCUMENTS

| | | |
|---|---|---|
| JP | 10-298385 A | 11/1998 |
| JP | 2003-315167 A | 11/2003 |
| JP | 2005-164528 A | 6/2005 |
| JP | 2006-133190 A | 5/2006 |
| JP | 2008-233909 A | 10/2008 |

OTHER PUBLICATIONS

International Search Report (PCT/ISA/210) issued in PCT Application No. PCT/JP2016/071476 dated Oct. 4, 2016 with English translation (2 pages).
Japanese-language Written Opinion (PCT/ISA/237) issued in PCT Application No. PCT/JP2016/071476 dated Oct. 4, 2016 (4 pages).
Extended European Search Report issued in counterpart European Application No. 16841324.3 dated May 3, 2019 (seven (7) pages).

* cited by examiner

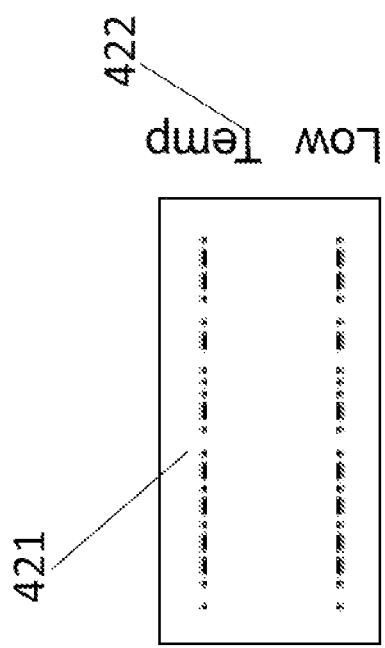

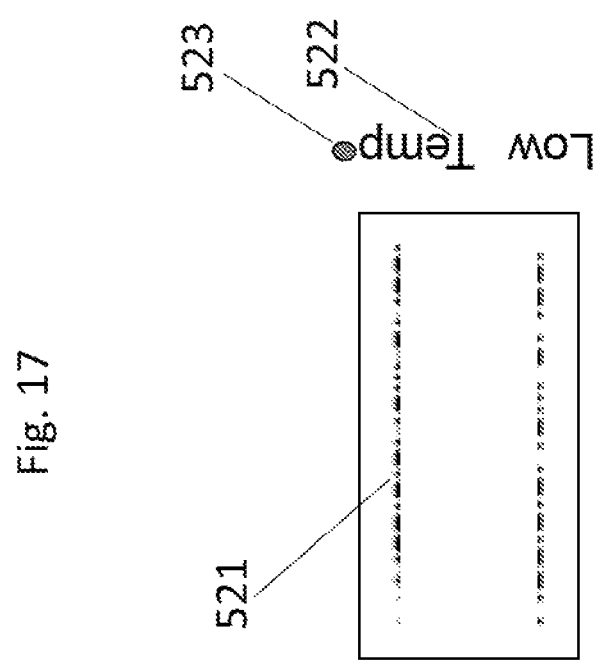

TEMPERATURE HISTORY INDICATOR

TECHNICAL FIELD

The present invention relates to a temperature history indicator, which displays the information of a fact that the temperature history indicator has been subjected to a certain temperature or lower.

BACKGROUND ART

In the world, so many commodities such as pharmaceuticals and foods are necessary to be stored within a certain temperature range. Such commodities are manufactured in factories and then transported to customers such as hospitals, supermarkets, and wholesalers by vehicles having a refrigerator function. Some commodities are temporarily stored in a warehouse in a factory and then transported to a customer.

The commodity must be kept at an appropriate temperature during transportation or storage in order to prevent degeneration of the commodity. For example, pharmaceuticals kept at inappropriate temperature lead to problems such as a reduction in medicinal effect, production of a harmful substance, and an increase in the harmful substance. Foods kept at an inappropriate temperature also lead to problems such as deterioration in taste or flavor due to denaturation.

In the European Union (EU), therefore, Good Distribution Practice of Medical Products for Human Use (2013/C68/01), which provides appropriate temperature control and the like for pharmaceuticals, has been executed since September 2013. As a result, real-time control using a temperature sensor and recording using a pen recorder or the like have been performed for temperature control in a container for pharmaceuticals transportation. Such control is available when a significant number of commodities are collectively transported from a factory. However, when one or several commodities are individually transported from a wholesaler to a hospital and the like, such strict control is difficult in light of both the staff and cost.

A display is therefore now investigated so that when temperature is deviated from a storage temperature, the information indicating such deviation can be displayed. In such a display, if the storage temperature is optimum, no color is developed, but if the storage temperature is lower than the optimum, a color is developed, and even if temperature rises again, the developed color does not disappear. A display with such a temperature tracer function is provided on a commodity or a package of the commodity, thereby when the commodity is exposed to an atmosphere below the storage temperature, such a temperature history remains.

Patent Literature 1 discloses an irreversible heat fading indicator for temperature history detection, in which a heat fading layer including a quasi-reversible heat fading material is provided. The indicator is designed such that when temperature is equal to or lower than a certain temperature, indication of "cold storage at optimum temperature" disappears and "out of optimum storage temperature" is displayed to inform that temperature becomes equal to or lower than the certain temperature or lower.

Patent Literature 2 discloses a reversible temperature-indicating element including a support and a temperature-indicating layer, which is switchable between a transparent state and a cloudy state according to a temperature change, on the support.

CITATION LIST

Patent Literature

Patent Literature 1: Japanese Unexamined Patent Application Publication No. 2003-315167.
Patent Literature 2: Japanese Unexamined Patent Application Publication No. Hei 07(1995)-027633.

SUMMARY OF INVENTION

Technical Problem

In the heat fading indicator disclosed in Patent Literature 1, whether temperature is equal to or lower than the certain temperature is visually checked. Such information is necessary to be individually entered to be converted into data. Such visual check and individual entry disadvantageously increase a possibility of a check error and a typing error. In addition, a workload increases, and thus workability of data entry is deteriorated.

The temperature-indicating element disclosed in Patent Literature 2 includes a material that becomes cloudy at a high temperature of 75.5° C. or higher. Hence, the temperature-indicating element can detect that temperature has exceeded a keeping temperature, but cannot detect that the temperature has become lower than the keeping temperature.

In light of such circumstances, it is intended to provide a temperature history indicator, in which a fact that temperature has been equal to or lower than a predetermined temperature can be visually confirmed and easily converted into data.

Solution to Problem

To solve the problem, a temperature history indicator of the present invention includes a label layer and a temperature-indicating layer laminated above or below the label layer, in which the temperature-indicating layer includes a substance having a crystallization start temperature of 10° C. or lower and a melting point at least 20° C. higher than the crystallization start temperature.

Advantageous Effects of Invention

According to the present invention, a temperature history indicator can be provided, in which the fact that temperature has been equal to or lower than the predetermined temperature can be visually confirmed and easily converted into data. Other issues, configurations, and effects are clarified by the description of the following embodiments.

BRIEF DESCRIPTION OF DRAWINGS

FIG. 16 is a top view of the temperature history indicator of Example 6 when temperature reaches a predetermined temperature or lower.

FIG. 17 is a top view of a temperature history indicator of Example 7 when temperature reaches a predetermined temperature or lower.

DESCRIPTION OF EMBODIMENTS

Hereinafter, some embodiments of the present invention will be described with reference to drawings.

Figure 1:
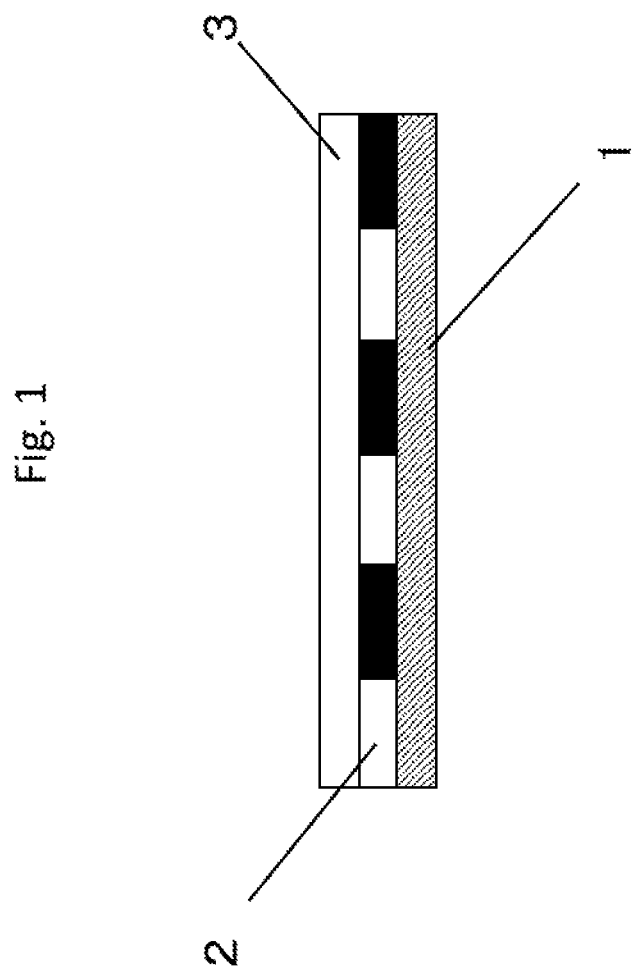
FIG. 1 is a sectional view of a temperature history indicator of one embodiment of the present invention.

FIG. 1 is a sectional view of a temperature history indicator of one embodiment of the present invention. In FIG. 1, the temperature history indicator includes a substrate 1, a label layer 2 laminated on the substrate 1, and a temperature-indicating layer 3 laminated on the label layer 2. The temperature-indicating layer 3 includes a substance having a crystallization start temperature of 10° C. or lower and a melting point at least 20° C. higher than the crystallization start temperature. The temperature-indicating layer 3 becomes cloudy (is reduced in transparency) through crystallization at a predetermined temperature or lower. As a result, display of the label layer 2 under the temperature-indicating layer 3 becomes invisible.

Figure 2:
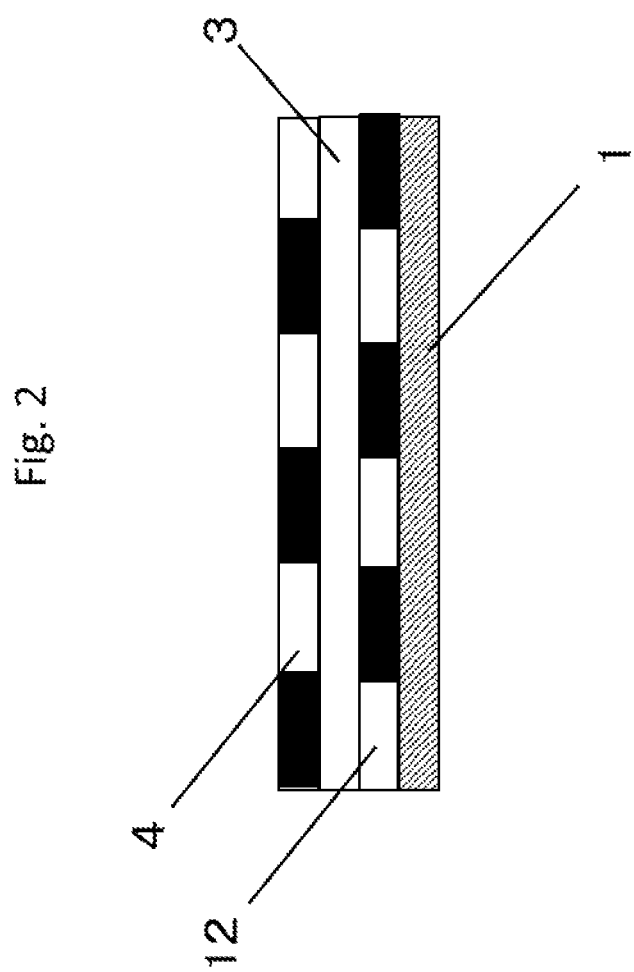
FIG. 2 is a sectional view of a temperature history indicator of another embodiment of the present invention.

FIG. 2 shows a sectional view of a temperature history indicator of another embodiment of the present invention. A first label layer 12 is formed on the substrate 1. A temperature-indicating layer 3 coloring at a certain temperature or lower lies on the first label layer 12. A second label layer 4 is formed on the temperature-indicating layer 3. The term "coloring" of the temperature-indicating layer 3 means coloring from transparency to white, white to black, white to red, or the like. In this specification, transparency means a haze value of 5% or less, which is determined by a haze meter, as defined by JIS K 7136 as a standard number of Japanese Industrial Standards (JIS).

For example, paper, film, or metal can be used for the substrate 1. When film is used, a material such as polyethylene or polypropylene is preferred because of low cost and tolerability to various organic solvents. When solvent resistance or adhesiveness is required, a film made of polyethylene terephthalate (PET) is preferred. It is also possible to form the label layer and the like directly on a product without the substrate 1. This can eliminate the effort to attach a produced temperature tracer, making it easy to use the temperature history indicator.

At least one of the label layers such as the first label layer 12 and the second label layer 4 included in the temperature history indicator is a read code such as a barcode printed by an inkjet method or the like. The code is preferably a mechanically readable optical code. The code may be either a one-dimensional code or a two-dimensional code. Types of the barcode may include JAN(EAN), CODE39, ITF, NW-7, CODE128, UPC, CODE93, and INDUSTRIAL 2 OF 5. An appropriate type of the barcode can be used according to the standard rules for products. The usable two-dimensional code may include a matrix-type two-dimensional code and a stack-type two-dimensional code.

The printing method includes the inkjet method, a direct printing method with a laser marker, and a method of attaching a printed matter that has been printed on a tape or the like. When information can be directly printed on a product by the inkjet method, the substrate is unnecessary, and no temperature tracer is necessary to be attached later, which are effective in cost reduction.

The temperature-indicating layer 3 includes a substance as a temperature-indicating material, which has a crystallization start temperature of 10° C. or lower and a melting point at least 20° C. higher than the crystallization start temperature. A specific configuration is different depending on a coloring color, or keeping temperature of a commodity.

Water, alcohols, esters, or a mixture thereof can be used as the temperature-indicating material. Such a material begins crystallization at a certain temperature or lower, and is thus whitened.

Examples of the alcohols include methyl alcohol, ethyl alcohol, iso-propyl alcohol, octanol, lauryl alcohol, cetyl alcohol, myristyl alcohol, stearyl alcohol, oleyl alcohol, and linoleyl alcohol.

Examples of the esters include 4-tert-butyl(cetyl benzoate), 4,4'-(hexa-fluoro-isopropylidene)bisphenol-dimyristate, stearyl caprylate, stearyl laurate, stearyl phosphate, neopentylglycol-dipalmitate, lauryl stearate, di-myristyl adipate, di-myristyl malonate, di-myristyl glutarate.

Figure 3:
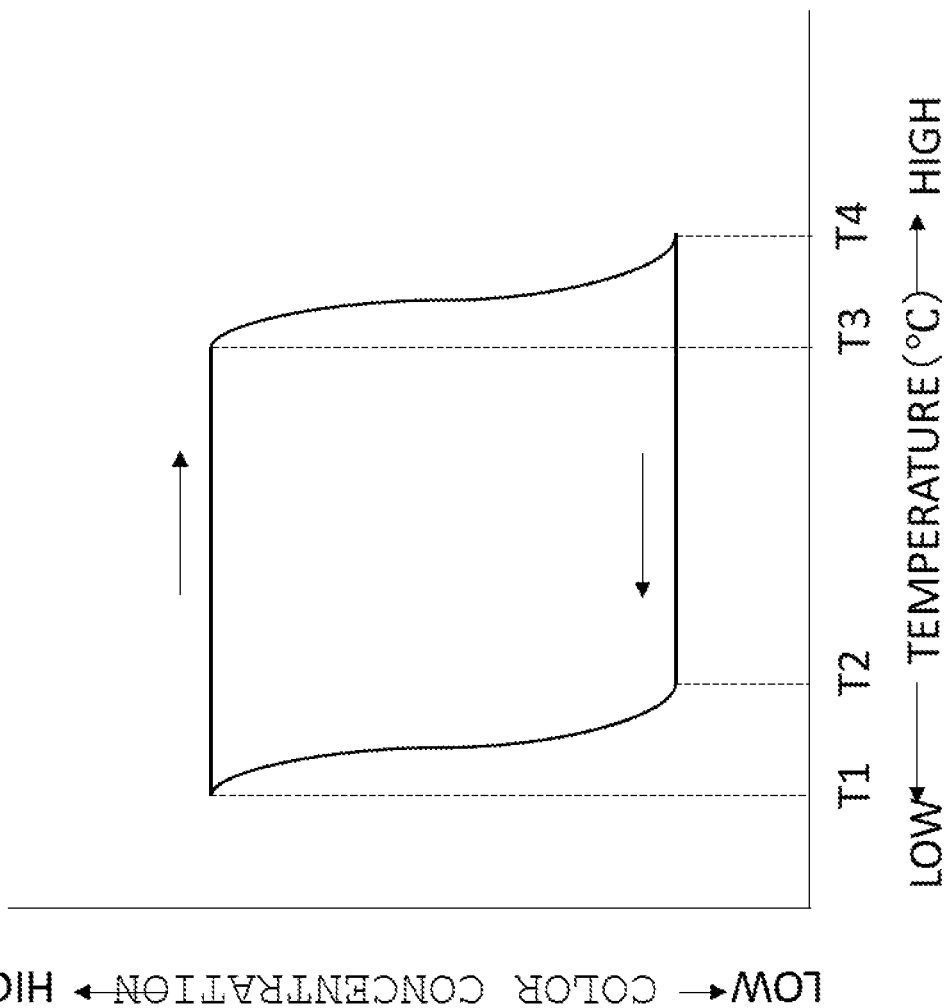
FIG. 3 is a diagram illustrating a relationship between temperature and coloring concentration of a temperature-indicating layer of the temperature history indicator of the one embodiment of the present invention.

An appropriate material is selected from such alcohols or esters to allow the solidification (crystallization) start temperature T2 to be different from the melting (transparency) start temperature T3 as shown in FIG. 3. As a result of this, once temperature becomes a certain temperature or lower, the material becomes cloudy (whitens), and as long as the temperature does not increase to the melting start temperature or higher, the material does not become transparent, leading to memory of the information of the fact that a low temperature has been detected. Such a temperature difference between T2 and T3 is preferably as large as possible. The temperature difference is at least 20° C. or more, and preferably 30° C. or more. If the temperature difference is small, the information of the fact that temperature has been lowered disappears by heating to a high temperature.

When a temperature-indicating layer that whitens from transparency is used, the temperature-indicating layer includes a material that is liquid at room temperature. A structure to support the material is therefore necessary. Such a structure must be transparent to allow the label layer to be read. Hence, the temperature-indicating layer preferably has a structure in which a temperature-indicating material is enclosed by a holding film such as a polymer film. The holding film may have a pouch structure. The polymer film includes polyethylene, polypropylene, and the like from the viewpoint of high transparency. When solvent resistance or adhesiveness is required, a film made of polyethylene terephthalate (PET) is preferred. A material that whitens at a low temperature is injected into a pouch structure of such a film, and is sealed. It is also possible to insert a spacer between two films to make a gap uniform, and inject a material that whitens at a low temperature into the gap.

A substance that develops or changes a color at a predetermined temperature or lower may be added in the temperature-indicating layer in addition to the temperature-indicating material. The addition of the substance that develops or changes a color at the predetermined temperature or lower allows coloring of the temperature-indicating layer when temperature becomes the predetermined temperature or lower. Examples of the substance that develops or changes a color at the predetermined temperature or lower may include leuco dye. In such a case, the temperature-indicating layer includes microcapsules containing alcohols, esters, phenols, and leuco dye. In this case, the low-temperature coloring layer may be formed in a form of a solid at room temperature. The alcohols and the esters are the same as those as described above, and an appropriate material can be variously selected from such materials. The phenols act as a developer for coloring of the leuco dye.

The phenols means materials having a phenolic hydroxyl group. Such materials include phenol, o-cresol, p-ethylphenol, butylphenol, 2,6-di(t-butyl)-4-methylphenol, nonylphenol, dodecylphenol, propyl gallate, iso-octyl gallate, n-octyl gallate, n-decyl gallate, n-cetyl gallate, methyl-4-hydroxybenzoate, ethyl-4-hydroxybenzoate, propyl-4-hydroxybenzoate, iso-octyl-4-hydroxybenzoate, n-dodecyl-4-hydroxybenzoate, o-phenylphenol, 5-aminonaphthol, 2,3-xylyl acid phosphate, bisphenol A, bis(4-hydroxyphenyl)methane, pyrocatechol, resorcin, hydroquinone, monochloro-o-phenylphenol, 2,4,6-trichlorophenol, pyrogallol, β-naphthol, 2,3-dihydroxynaphthalene, p-methoxyphenol, 4,4'-thio-bis-(6-t-butyl-3-methylphenol), 4,4'-(hexafluoroisopropylidene)diphenol, and 4,4'-(2-methyl-propylidene)bisphenol.

The leuco dye may include various dyes such as phthalide derivatives, carbinol derivatives, auramine derivatives, lactam derivatives, indoline derivatives, spiropyran derivatives, and fluoran derivatives. An appropriate dye can be selectively used in light of a desired color, light resistance, and the like.

Micro-encapsulation can be performed using a known method. For example, coacervation, interfacial polymerization, in situ polymerization, a cured coating method in liquid, an air-suspension coating method, and a spray dry method can be used. Two or more different methods can be used in combination without being limited to the above methods. Examples of a microcapsule wall film substance may include polyurea, polyamide, polyurethane, epoxy resin, melamine resin, urea formaldehyde resin, and vinyl resin. When the temperature-indicating layer is formed by the inkjet method using the ink including microcapsules, dispersibility of the microcapsules in the ink is necessary to be improved. To this end, a coupling agent can be appropriately formed in a microcapsule shape to improve the dispersibility. When printing is performed with an inkjet ink, size of the microcapsule must be sufficiently reduced to eliminate clogging in a head of an inkjet device. The size of the microcapsule must be at most 50 μm or less. The size is hopefully 10 μm or less. The surface of each microcapsule may be modified to prevent clogging of the microcapsules.

A protective film protecting the label layer may be formed on the label layer. When the protective film is formed, the film is necessary to be transparent or substantially transparent in a visible range such that the display can be read. As such a material, an amorphous material is more preferable than a highly crystalline material. Specifically, an amorphous PET resin, polycarbonate resin, acrylic resin, or the like is more preferable than a crystalline polymer such as polyethylene or polypropylene. However, the crystalline resin is also usable by forming a thin cover layer to improve light transmission.

It is an indispensable condition that the protective film material does not dissolve an underlayer such as the label layer. Further, when the protective film material is dissolved in an organic solvent or the like and applied on the formed label layer to form the protective film, the solvent dissolving the protective film material must be selected so as not to dissolve the underlayer such as the label layer.

Some examples of the present invention are now described.

Example 1

Figure 4:
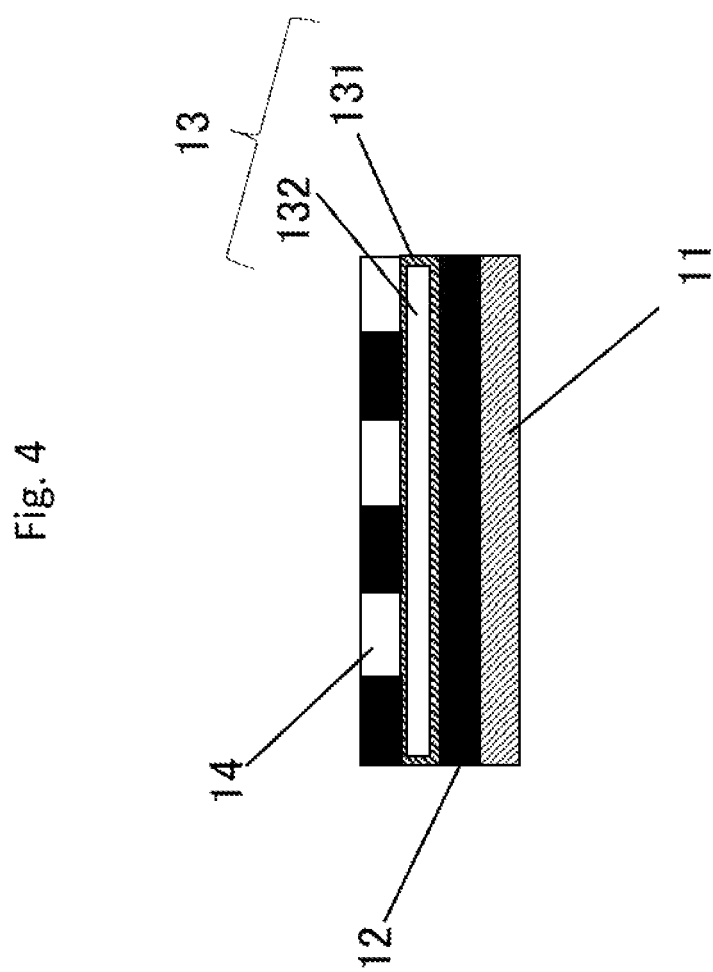
FIG. 4 is a sectional view of a temperature history indicator of Example 1.
Figure 5:
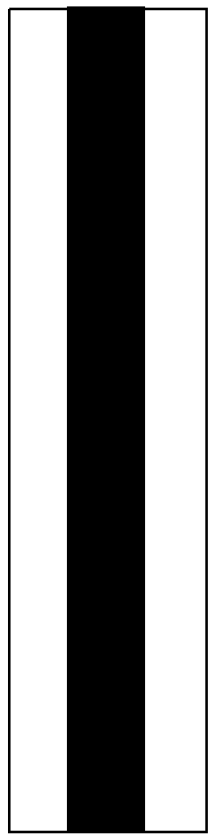
FIG. 5 is a top view of a second label layer in Example 1.
Figure 6:
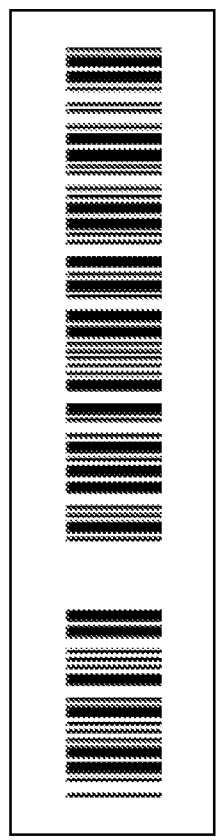
FIG. 6 is a top view of a first label layer in Example 1.

FIG. 4 illustrates a structure of a temperature tracer of Example 1. Paper was used for a substrate 11. A first label layer 12 was formed by printing a barcode by an inkjet method. BONJET BLACK CW1 (from ORIENT CHEMICAL INDUSTRIES CO., LTD.) was used as the black ink for the inkjet method. FIG. 5 illustrates a top view of the first label layer. The first label layer 12 was printed as shown in FIG. 5. Polyethylene was used for a holding film 131 configuring a temperature-indicating layer. Lauryl stearate was used as a temperature-indicating material 132. The lauryl stearate had a crystallization start temperature of 6° C. and a melting point of 41° C. The crystallization start temperature was determined by differential thermal analysis (DTA). An extrapolated crystallization start temperature was determined from a DTA curve by the method defined by JIS K 7121. Thickness of a low-temperature coloring material was about 10 μm. A barcode was formed as a second label layer 14 by an inkjet method. A CODE39 barcode was used. VALIFAST BLACK 3810 (from ORIENT CHEMICAL INDUSTRIES CO., LTD.) was used as the black ink for the inkjet method. FIG. 6 illustrates a top view of the second label layer. The second label layer 14 was printed as shown in FIG. 6. The barcode read as "*NG_LowTemp*" by a barcode reader was used as the second label layer.

Figure 7:
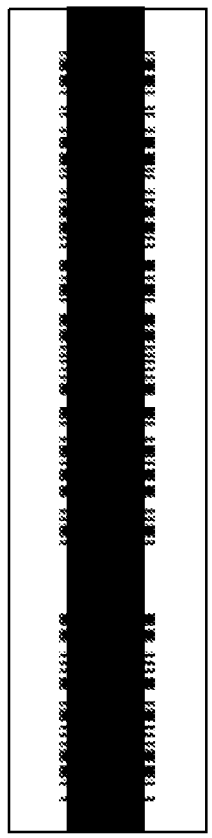
FIG. 7 is a top view of the temperature history indicator of Example 1.

The temperature tracer produced as above was attached to an article, and the article was left at room temperature. FIG. 7 illustrates a top view of a temperature history indicator of Example 1. The temperature history indicator left under room temperature was not able to be read by the barcode reader.

Figure 8:
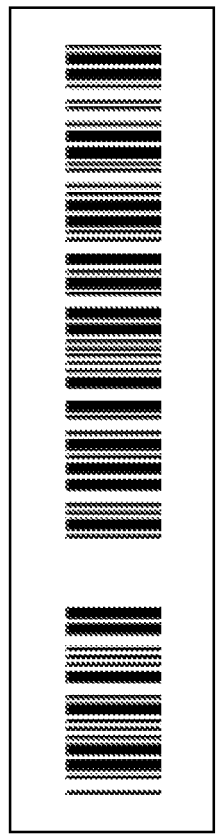
FIG. 8 is a top view of the temperature history indicator of Example 1 when temperature reaches a predetermined temperature or lower.

Subsequently, the temperature history indicator tracer of Example 1 was attached to an article, and the article was kept at 5° C. for 30 minutes. The temperature history indicator was then returned to room temperature. FIG. 8 illustrates a top view of such a temperature history indicator. The barcode can be read by the barcode reader. As a result of the reading, "*NG_LowTemp*" was given, showing that the temperature tracer had been subjected to 6° C. or lower. In this way, a fact that temperature has been equal to or lower than a certain temperature can be displayed by the temperature tracer of the present invention, read by a barcode reader, and simply converted into data.

Example 2

In Example 2, two or more indicators were used. The second example used a temperature history indicator (first temperature history indicator) having a temperature-indicating layer on which letters were displayed at a predetermined temperature or lower, and the temperature history indicator (second temperature history indicator) of Example 1.

Figure 9:
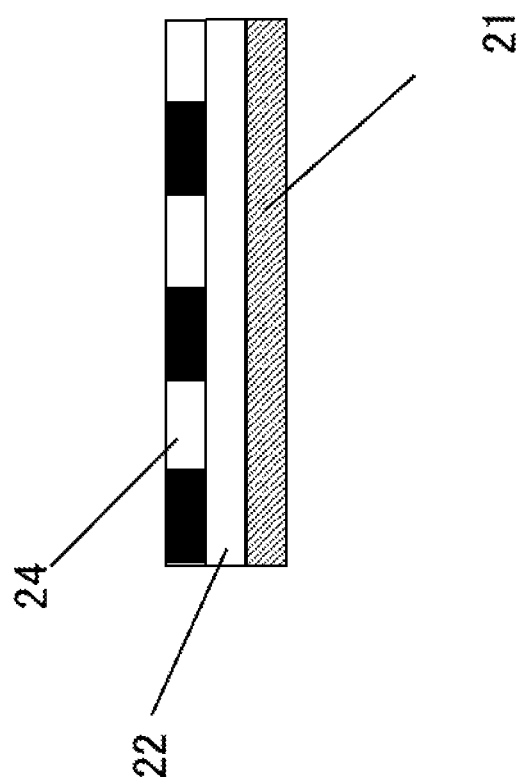
FIG. 9 is a sectional view of a first temperature history indicator of Example 2.

FIG. 9 illustrates a sectional view of the temperature history indicator having a temperature-indicating layer on which letters are displayed at a predetermined temperature or lower. The temperature history indicator includes a substrate 21, and a temperature-indicating layer 22 and a label layer 24 laminated on the substrate 21. Paper was used for the substrate 21. The temperature-indicating layer 22 was formed by printing an ink including microcapsules containing lauryl stearate, ethyl gallate, and 6-(diethylamino)-2-[(3-trifluoromethyl)aniline]xanthine-9-spiro-3'-phthalide by an inkjet method. The weight ratio of lauryl stearate, ethyl gallate, and 6-(diethylamino)-2-[(3-trifluoromethyl)aniline]xanthine-9-spiro-3'-phthalide was 24:2:1. Melamine resin was used as a microcapsule wall film material. Interfacial polymerization was used for micro-encapsulation. The above-described ink was used to produce a visually confirmable temperature-indicating layer, the printed portion of which was blackened and visually confirmed at a temperature of 6° C. or lower while being white at room temperature. In this example, printing was performed such that when the printed portion was blackened, letters "LOW TEMP" appeared.

Figure 10:
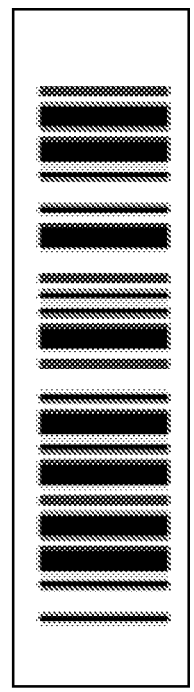
FIG. 10 is a top view of a label layer of the first temperature history indicator of Example 2.

The label layer 24 includes a code as shown in FIG. 10 printed by an inkjet method. The barcode, which is written in CODE39 format, can be read by a barcode reader. When the barcode is read, the information of "*OK*" can be recorded.

The produced temperature history indicator was attached to an article, and the article was kept at room temperature, and then read by the barcode reader. As a result of the reading of the first temperature history indicator, "*OK*" was given. However, the second temperature history indicator was not able to be read.

Figure 11:
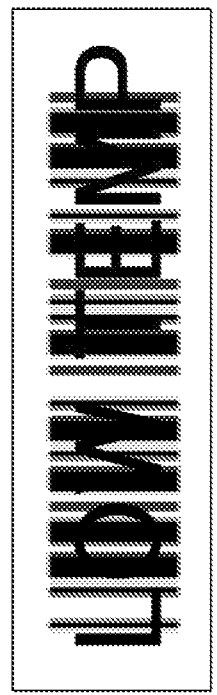
FIG. 11 is a top view of the temperature history indicator of Example 2 when temperature reaches a predetermined temperature or lower.

The article was kept for 30 minutes at 5° C., and each temperature history indicator was read by the barcode reader. The first temperature history indicator was shown as in FIG. 11 and thus not able to be read by the barcode reader. Since letters of LOW TEMP, which indicated that temperature had been low, appeared as shown in FIG. 11, it was able to be visually confirmed that the article had been subjected to 6° C. or lower. As a result of the reading of the second temperature history indicator, "*NG_LowTemp*" was given, showing that the article had been subjected to 6° C. or lower.

As described above, when two or more barcodes are used, the same type of barcodes are used, so that the need of successive change of read setting is eliminated, and the barcodes can be read and converted into data more easily.

Example 3

A temperature history indicator of Example 3 was produced in the same way as in Example 2 except that an ink containing lauryl stearate, ethyl gallate, and 2-methyl-6-(N-p-tolyl-N-ethylamino)-fluoran was used for the temperature-indicating layer of the first temperature history indicator of Example 2. In the temperature history indicator of Example 3, red letters "LOW TEMP" appear at a low temperature, leading to higher visibility. As a result, visual confirmation is easily performed.

Example 4

Figure 12:
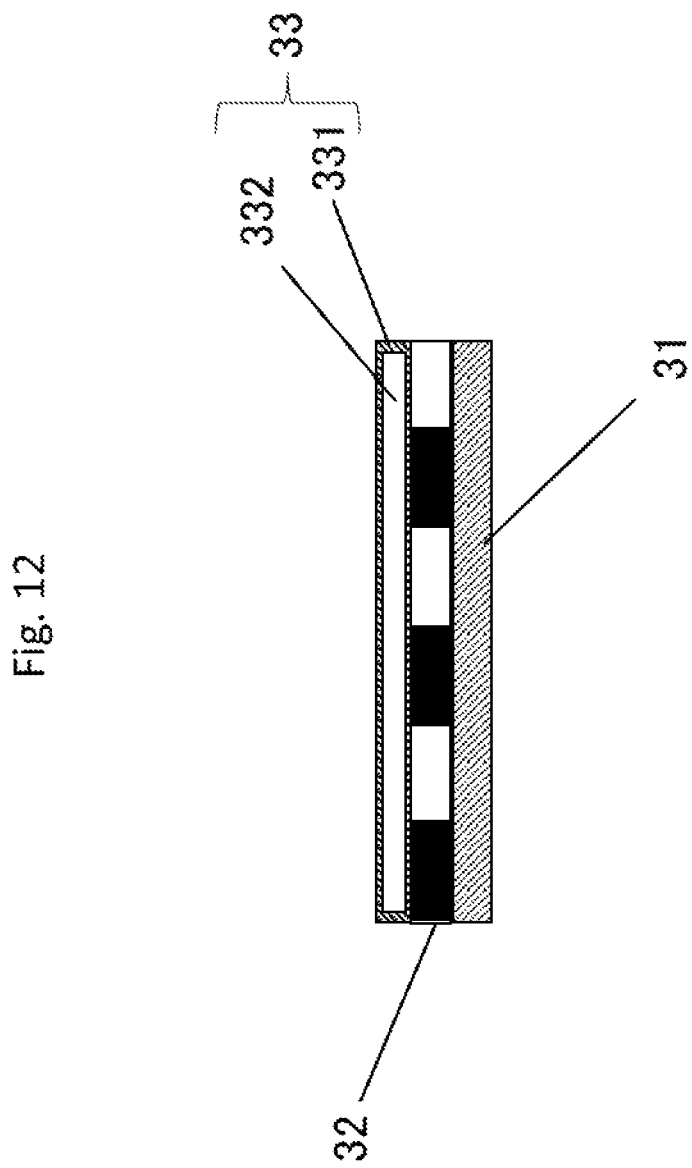
FIG. 12 is a sectional view of a temperature history indicator of Example 4.

FIG. 12 illustrates a sectional view of a temperature history indicator of Example 4. The temperature history indicator of Example 4 has a structure, in which a label layer 32 is laminated on a substrate 31, and a temperature-indicating layer 33 is laminated on the label layer. The temperature-indicating layer is configured such that a temperature-indicating material 332 is included in a film 331 for holding the temperature-indicating material.

Figure 13:
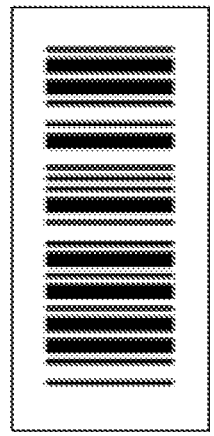
FIG. 13 is a top view of a label layer in Example 4.

Paper was used for the substrate 31. A barcode was printed as the label layer 32 by an inkjet method. The barcode is written in CODE39 format. FIG. 13 illustrates a top view of the label layer 32. When the barcode is read, the information of "*OK*" can be recorded. Polyethylene was used for the film 331. Lauryl stearate was used as the temperature-indicating material 332. Thickness of the temperature-indicating layer was about 5 μm.

Since the produced temperature history indicator had a transparent temperature-indicating layer, the label layer under the temperature-indicating layer was able to be read.

The temperature history indicator of Example 4 was attached to an article, and the article was kept at 5° C. for 30 minutes. Thirty minutes later, the temperature-indicating material 332 of the temperature history indicator was whitened, so that the label layer 32 was not able to be read. As described above, the temperature history indicator of Example 4 operates as a temperature tracer that detects a low temperature.

Example 5

In Example 5, a temperature history indicator was produced in the same way as in Example 1 except that myristyl alcohol was used as a temperature-indicating material. The myristyl alcohol had a crystallization start temperature of 4° C. and a melting point of 39° C. In the temperature history indicator of Example 4 at 4° C. or higher, since the temperature-indicating layer is transparent, the second label layer and the first label layer under the temperature-indicating layer are superposed each other, so that the barcode cannot be read. However, at 4° C. or lower, the temperature-indicating layer becomes cloudy, and the underlying first label layer becomes invisible. As a result, the barcode of the second label layer can be read.

The temperature history indicator was left in an atmosphere of 4° C. or lower, and then the barcode was read using a barcode reader. As a result of the reading, "*NG_LowTemp*" was given. As described above, it is possible to record the information of the fact that the temperature history indicator of Example 5 has been subjected to 4° C. or lower.

Example 6

Figure 14:
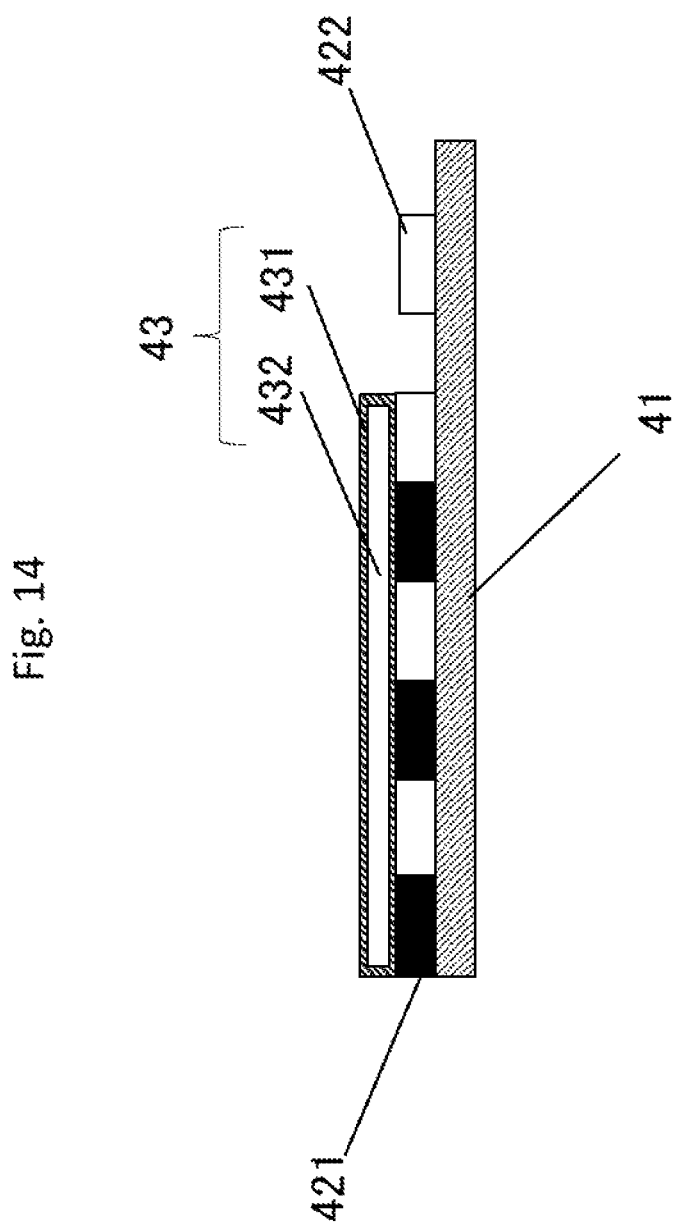
FIG. 14 is a sectional view of a temperature history indicator of Example 6.
Figure 15:
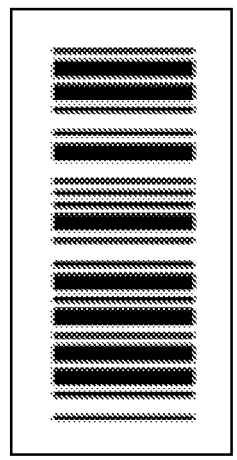
FIG. 15 is a top view of a label layer in Example 6.

FIG. 14 illustrates a structural view of a temperature tracer of Example 6. A label layer 421 and a temperature-indicating layer 43 are laminated on a surface of a substrate 41. A temperature-indicating label part 422 is also disposed on the surface of the substrate 41. Paper was used for the substrate 41. A barcode was printed as the label layer 421 by an inkjet method. The barcode was written in CODE39 format. BONJET BLACK CW1 (from ORIENT CHEMICAL INDUSTRIES CO., LTD.) was used as the black ink for the inkjet method. FIG. 15 illustrates a top view of the label layer 421. When the barcode is read by a barcode reader, the information of "*OK*" can be recorded. The temperature-indicating label part 422 was formed using an ink that is white at room temperature, and includes microcapsules containing lauryl stearate, ethyl gallate, and 6-(diethylamino)-2-[(3-trifluoromethyl)aniline]xanthine-9-spiro-3'-phthalide. The weight ratio of lauryl stearate, ethyl gallate, and 6-(diethylamino)-2-[(3-trifluoromethyl)aniline]

xanthine-9-spiro-3'-phthalide is 24:2:1. Melamine resin was used as a microcapsule wall film material. Interfacial polymerization was used for micro-encapsulation. When the temperature-indicating label part 422 is subjected to 6° C. or lower, a black display of "Low Temp" can be visually confirmed. Polyethylene was used for the temperature-indicating-material holding film 431. Lauryl stearate was used as a temperature-indicating material 432. The thickness of the temperature-indicating layer was about 10 μm. When an article, to which the temperature tracer of Example 6 has been attached, is kept at room temperature, the barcode of the label layer 421 is directly read. When the article, to which the temperature tracer of Example 6 has been attached, is kept at 5° C. for 30 minutes, a display as shown in FIG. 16 is given. As a result of this, the barcode cannot be read by the barcode reader, and thus the information of "*OK*" is not entered. Further, the information of "Low Temp" can be visually confirmed aside. As described above, the information showing that the temperature tracer has been subjected to a certain temperature or lower can be entered and visually recognized.

Example 7

A temperature tracer of Example 7 is the same as that of Example 6 except for the following point. A label layer 521 and a temperature-indicating layer are laminated on a surface of a substrate. A first temperature-indicating label part 522 and a second temperature-indicating label part 523 are also disposed on the surface of the substrate.

The label layer 521, the temperature-indicating layer, and the first temperature-indicating label part 522 are the same as those of Example 6. The second temperature-indicating label part 523 was formed. The second temperature-indicating label part 523 was printed using an inkjet method. The used ink included microcapsules containing lauryl stearate, ethyl gallate, and 2-methyl-6-(N-p-tolyl-N-ethylamino)-fluoran. The weight ratio of lauryl stearate, ethyl gallate, and 2-methyl-6-(N-p-tolyl-N-ethylamino)-fluoran is 24:2:1. Melamine resin was used as a microcapsule wall film material. Interfacial polymerization was used for micro-encapsulation. The print of the second temperature-indicating label part 523 is colored red at 6° C. or lower, and the information can be read using a special reader.

When an article to which the temperature tracer of Example 7 is attached is kept at 5° C. for 30 minutes, a display is given as shown in FIG. 17. The barcode of the label layer is not readable. The information of "Low Temp" first temperature-indicating label part on the side can be visually confirmed. The code of the second temperature-indicating label part 523 appears and is read by a reader, thereby the information of "NG_Low Temp" can be entered without manual entry.

LIST OF REFERENCE SIGNS 1, 11, 21, 31, 41 . . . Substrate
2, 24, 32, 423, 521 . . . Label layer
12 . . . First label layer
3, 13, 33, 43 . . . Temperature-indicating layer
4, 14 . . . Second label layer
131, 331, 431 . . . Holding film
132, 332, 432 . . . Temperature-indicating material
422, 522 . . . First temperature-indicating label part
523 . . . Second temperature-indicating label part

The invention claimed is:

1. A temperature history indicator, comprising:
 a label layer;
 a first temperature-indicating layer laminated on a substrate above or below the label layer,
 wherein the first temperature-indicating layer includes a substance having a crystallization start temperature of 10° C. or lower and a melting point at least 20° C. higher than the crystallization start temperature,
 wherein the label layer displays one of a one-dimensional code and a two-dimensional code; and
 a second temperature-indicating layer which is disposed on the substrate but is not stacked on the label layer and the first temperature-indicating layer.

2. The temperature history indicator according to claim 1, wherein the first temperature-indicating layer becomes cloudy at the crystallization start temperature or lower, thereby the label layer becomes readable or unreadable.

3. The temperature history indicator according to claim 1, wherein the first temperature-indicating layer includes one of esters, alcohols, and water.

4. The temperature history indicator according to claim 1, wherein the first temperature-indicating layer includes a substance that develops or changes a color at a predetermined temperature or lower.

5. The temperature history indicator according to claim 4, wherein the first temperature-indicating layer includes microcapsules containing phenols and leuco dye.

6. The temperature history indicator according to claim 4, wherein the first temperature-indicating layer develops or changes a color to display information indicating that the temperature history indicator has been placed in an atmosphere of a predetermined temperature or lower.

7. The temperature history indicator according to claim 1, wherein the first temperature-indicating layer has a structure in which a substance having the crystallization start temperature of 10° C. or lower and the melting point at least 20° C. higher than the crystallization start temperature is enclosed by a holding film.

8. The temperature history indicator according to claim 1, wherein the label layer includes a first label layer and a second label layer, and
 the first temperature-indicating layer is disposed between the first label layer and the second label layer.

9. The temperature history indicator according to claim 1, wherein the label layer and the first temperature-indicating layer are laminated on a surface of the substrate.

10. The temperature history indicator according to claim 9, wherein a color of the second temperature-indicating layer changes at a temperature that is less than or equal to a prescribed temperature.

\* \* \* \* \*